US012274787B2

(12) United States Patent
Lee et al.

(10) Patent No.: US 12,274,787 B2
(45) Date of Patent: Apr. 15, 2025

(54) SUSTAINED-RELEASE INJECTION COMPRISING DESLORELIN, AND PREPARATION METHOD THEREFOR

(71) Applicant: G2GBIO, INC., Daejeon (KR)

(72) Inventors: Heeyong Lee, Daejeon (KR); Eunyoung Seol, Daejeon (KR); Yongha Na, Daejeon (KR); Juhan Lee, Daejeon (KR)

(73) Assignee: G2GBIO, INC., Daejeon (KR)

( * ) Notice: Subject to any disclaimer, the term of this patent is extended or adjusted under 35 U.S.C. 154(b) by 790 days.

(21) Appl. No.: 17/312,061

(22) PCT Filed: Dec. 17, 2019

(86) PCT No.: PCT/KR2019/017905
§ 371 (c)(1),
(2) Date: Jun. 9, 2021

(87) PCT Pub. No.: WO2020/130585
PCT Pub. Date: Jun. 25, 2020

(65) Prior Publication Data
US 2022/0023217 A1 Jan. 27, 2022

(30) Foreign Application Priority Data
Dec. 17, 2018 (KR) .................. 10-2018-0163416

(51) Int. Cl.
*A61K 38/09* (2006.01)
*A61K 9/16* (2006.01)

(52) U.S. Cl.
CPC .......... *A61K 9/1647* (2013.01); *A61K 9/1682* (2013.01); *A61K 38/09* (2013.01)

(58) Field of Classification Search
CPC ..... A61K 38/09; A61K 9/1647; A61K 9/0019
See application file for complete search history.

(56) References Cited

U.S. PATENT DOCUMENTS

| 6,270,700 B1 * | 8/2001 | Ignatious | A61K 9/1694 264/4.1 |
| 2011/0200679 A1 | 8/2011 | Lim et al. | |
| 2017/0273911 A1 * | 9/2017 | Walsh | A61M 25/0043 |

FOREIGN PATENT DOCUMENTS

| CN | 102137657 | 7/2011 |
| EP | 2327397 | 6/2011 |
| EP | 2134329 | 1/2015 |
| EP | 3949951 | 2/2022 |
| JP | S 63-41416 | 2/1988 |
| JP | 2002-020269 | 1/2002 |
| JP | 2010-522743 | 7/2010 |
| JP | 2014-224114 | 12/2014 |
| JP | 2015-086136 | 5/2015 |
| JP | 2016-515612 | 5/2016 |
| KR | 10-0722607 | 5/2007 |
| KR | 10-2010-0026384 | 3/2010 |
| KR | 10-2013-0070353 | 6/2013 |
| KR | 10-2013-0100464 | 9/2013 |
| KR | 10-1583351 | 1/2016 |
| KR | 10-1663561 | 10/2016 |
| KR | 10-2185348 | 12/2020 |
| WO | 2008-066279 | 6/2008 |
| WO | 2008-117927 | 10/2008 |
| WO | 2013-094955 | 6/2013 |

OTHER PUBLICATIONS

KIPO, A PCT Search Report & Written Opinion of PCT/KR2019/017905, dated Apr. 13, 2020.
JPO, Decision of Rejection of JP 2021-507691 dated Dec. 17, 2018.
SIPO, Office Action of the corresponding Chinese Patent Application No. 201980092245.2 dated Aug. 8, 2022.
Yu Li, et al. "Effects of Different Grades of PLGA on Encapsulation Efficiency and in vitro Release Behavior of Octreotide Microspheres", Chinese Journal of Pharmaceuticals, vol. 43, issue 1, pp. 39 to 42, Dec. 31, 2012.
JPO, Office Action of JP 2021-507691 dated Feb. 15, 2022.
Deepak N. Kapoor et al., "Development and optimization of in-situ forming microparticles for long term controlled delivery of deslorelin acetate", Journal of Applied Pharmaceutical Science, Jan. 2018, and vol. 8 and pp. 59-72.
Fredenberg, Susanne, et al. "The mechanisms of drug release in poly (lactic-co-glycolic acid)-based drug delivery systems—A review." International journal of pharmaceutics 415.1-2 (Aug. 30, 2011): 34-52.
Rowe, Raymond C., et al. Handbook of pharmaceutical excipients. the Pharmaceutical Press & the American Pharmacists Association, 6th edition (2009), excerpt from pp. 515-517.
KIPO, Applicant reply (Written Opinion) submitted to KIPO of the Patent Application No. KR 10-2019-0169203 dated Sep. 5, 2020.
JPO, Applicant reply (Written Opinion) submitted to JPO of the Patent Application No. JP 2021-507691 dated Aug. 12, 2022.
JPO, Decision of Refusal of the Japanese Patent Application No. 2021-507691, Nov. 28, 2022.
Lin, Jiunn H. "Species similarities and differences in pharmacokinetics." Drug Metabolism and Disposition 23.10 (Oct. 1, 1995): 1008-1021.
Toutain, Pierre-Louis, et al. "Species differences in pharmacokinetics and pharmacodynamics." in F. Cunningham et al. (eds.), Comparative and Veterinary Pharmacology, Handbook of Experimental Pharmacology 199, Springer-Verlag Berlin Heidelberg (2010): 19-48.
SIPO, Office Action of CN 2019800922452 dated Feb. 26, 2023.

(Continued)

*Primary Examiner* — Johann R Richter
*Assistant Examiner* — Danielle Johnson
(74) *Attorney, Agent, or Firm* — LEX IP MEISTER, PLLC (57) ABSTRACT

The present disclosure relates to a sustained-release injection formulation comprising biodegradable polymer microspheres containing deslorelin as an active ingredient, and a preparation method therefor. The sustained-release microsphere injection containing deslorelin, according to the present disclosure, has good administrability and enables, with a single administration, a deslorelin drug to be maintained at an effective concentration for 6 months without rapid temporary release into the blood of an animal.

3 Claims, 1 Drawing Sheet

(56) References Cited

OTHER PUBLICATIONS

EPO, third-party observations filed anonymously of the corresponding European Patent Application No. 19900868.1 dated May 11, 2023.
EPO, the office action of the corresponding European Patent Application No. 19900868.1 dated Jul. 7, 2023.
Bowen, Paul. "Particle size distribution measurement from millimeters to nanometers and from rods to platelets." Journal of dispersion science and technology 23.5 (Jan. 11, 2002): 631-662.
JPO, Pending claims of the corresponding Japanese Patent Application No. JP 2021-507691 dated Aug. 12, 2022.
James G.W. Wenzel et al., "Pluronic0® F127 gel formulations of Deslorelin and GnRH reduce drug degradation and sustain drug release and effect in cattle", Journal of Controlled Release, (Dec. 12, 2002), vol. 85, pp. 51-59.
EPO, Search Report of EP 19900868.1 dated May 17, 2022.
Susanne Fredenberg et al., "The mechanisms of drug release in poly(lactic-co-glycolic acid)-based drug delivery systems—A review", Int J Pharm. Aug. 30, 2011;415(1-2):34-52. doi: 10.1016/j.ijpharm.2011.05.049. Epub May 27, 2011. PMID: 21640806.
Handbook of Pharmaceutical Excipients Sixth Edition (2009) paragraph [0018] p. 516.
Jiunn H. Lin. "Species similarities and differences in pharmacokinetics", Drug Metab Dispos. Oct. 1995;23 (10):1008-21. PMID: 8654187.
Pierre-Louis Toutain et al., "Species Differences in Pharmacokinetics and Pharmacodynamics", Handb Exp Pharmacol. 2010;(199):19-48. doi: 10.1007 /978-3-642-10324-7_2. PMID: 20204582.
Yu Li, Li Minzhi et al., "Effect of different PLGA models on octreotide microsphere encapsulation efficiency and in vitro release behavior", Chinese Journal of Pharmaceuticals, 2012, vol. 43, No. 1, p. 39-43.
Neelesh K Varde et al., "Microspheres for controlled release drug delivery", Expert Opin Biol Ther. Jan. 2004;4(1):35-51. doi: 10.1517 /14712598.4.1 .35. PMID: 14680467.
Communication pursuant to Article 94(3) EPC' (examination report) issued by the European Patent Office on Jul. 7, 2023 in respect of EP3900705.
James G.W Wenzel et al: "PluronicA(R) F127 gel formulations of Deslorelin and GnRH reduce drug degradation and sustain drug release and effect in cattle", Journal of Controlled Release, vol. 85, No. 1-3, Dec. 13, 2002, pp. 51-59, XP004397765, ISSN: 0168-3659, DOI: 10.1016/S0168-3659(02)00271-7.
IP Australia, 3rd party notice of AU 2019401868 dated Aug. 15, 2023.
EPO, Office Action of EP 19900868.1 dated May 27, 2024.
Kavitha Koushik et al., "Preparation of large porous deslorelin-PLGA microparticles with reduced residual solvent and cellular uptake using a supercritical carbon dioxide process", Pharmaceutical Research, vol. 21, No. 3, Mar. 2004, pp. 524-535.
Kavitha Koushik et al., "Pulmonary Delivery of Deslorelin: Large-Porous PLGA Particles and HPβCD Complexes", Pharmaceutical Research, vol. 21, No., 7, Jul. 2004, pp. 1119-1126.
EPO, Office Action of EP 19900868.1 dated Feb. 11, 2025, total 10 pages.
EPO, Third Party Observation of EP 19900868.1 dated Jan. 8, 2025, total 9 pages.
EPO, Third Party Observation of EP 19900868.1 dated Feb. 5, 2025, total 3 pages.

* cited by examiner

SUSTAINED-RELEASE INJECTION COMPRISING DESLORELIN, AND PREPARATION METHOD THEREFOR

CROSS-REFERENCE TO RELATED APPLICATION(S)

This application claims the benefit of Korean Patent Application No. 10-2018-0163416 filed on Dec. 17, 2018 with the Korean Intellectual Property Office, the disclosure of which is incorporated herein by reference in its entirety.

TECHNICAL FIELD

The present disclosure relates to a biodegradable microsphere injection formulation comprising deslorelin and a method for preparing the same.

BACKGROUND ART

The present disclosure relates to a sustained release formulation and a veterinary formulation of deslorelin, which is an agonist of a peptide gonadotropin-releasing hormone. The use of the formulations includes the prevention of reproductive function, especially in dogs and cats, and the treatment of prostate and breast cancer and other diseases or conditions for which inhibition of testosterone or estradiol levels is beneficial.

Unauthorized breeding of pets is a global problem, and it is very difficult to control the breeding of dogs and cats, especially in developing countries. Surgical castration is aimed at reproductive regulation of these animals. However, surgical operation, no matter how minor, carries risks. Many pet owners are reluctant to neutralize their pets with surgical procedures.

Therefore, the peptide gonadotropin-releasing hormone is often used for the purpose of inhibiting reproductive functions and other processes that are affected by sex hormone levels.

Industrially, for the success of a non-surgical neutralizing agent for pets, it should be effective in all animals and the sex hormone inhibition period should be predictable. The sex hormone suppression period should last for 6 months. That is, it is necessary to have an efficient drug delivery system in which peptide drugs are released for 6 months or more at a regulated rate and dose that can block the secretion of sex hormones in animals in a predictable and stable manner. The reversibility of the inhibitory effect is an additional desirable advantage compared to surgical operation.

Peptech Animal Health in Australia have developed a lipid implant containing deslorelin (brand name: Suprelorin; vendor: Virbac, France) and sold as 6- and 12-month formulations for chemical castration in male dogs. However, Suprelorin is an implant formulation and has the disadvantage of requiring the use of thick injection needle when injecting to animals (6-month formulation: 12 gauge, 12-month formulation: 11 gauge). Further, it is known that the effects of drugs appear late in the early stage, and the duration of the drug is not constant. For this reason, it was not approved for neutralization applications in female dogs or cats.

Therefore, there is a need to develop a deslorelin sustained-release injection formulation in which when administered to pets such as dogs and cats, the initial drug release of deslorelin is sufficient, and also the drug is released constantly and stably for a certain period of time, for example, for 6 months or more, and after a certain period of time, the drug release is completed.

The present inventors have developed a sustained-release formulation containing deslorelin as an active agent in which the effect of the initial drug is expressed early when administered to an animal and inhibits reproductive function over a predictable period of time. The formulation is also a reversible neutralizing agent in which reproductive function is restored after the end of the drug release period after administration. The deslorelin formulation according to the present disclosure is useful for treating a range of hormone-dependent diseases and conditions in animals, especially pets such as dogs and cats. The formulation according to the present disclosure allows deslorelin to be administered once every 6 months, and thereby reduce the need for frequent subcutaneous injections or implant insertions and provide an improved therapy for treating hormone-dependent diseases and conditions in animals.

DETAILED DESCRIPTION OF THE INVENTION

Technical Problem

The present disclosure has been devised to solve the problem of deslorelin implant formulations in addition to neutralization by conventional surgical operations as described above, and it is an object of the present disclosure to provide a deslorelin sustained-release microsphere in which the initial release amount of the deslorelin drug is sufficient and also it exhibits the characteristics of stable drug release for 6 months or more and releases more than 85% of the drug administered for 6 months or more, and a method for preparing the same.

Technical Solution

In order to achieve the above objects, one embodiment of the present disclosure provides a deslorelin-containing sustained-release microsphere injection formulation which uses two or more polymers selected from the group consisting of poly(lactide-co-glycolide) and polylactide polymers having a lactide-to-glycolide ratio of 50:50 to 100:0 and an intrinsic viscosity of 0.16 to 1.20 dL/g, wherein a content of deslorelin is 5 to 25% by weight based on the total weight of the microsphere, and a method for preparing the same.

Another embodiment of the present disclosure provides a deslorelin sustained-release microsphere injection formulation having good administrability, with the deslorelin sustained-release microsphere having an average particle size of 10 μm to 100 μm, and a method for preparing the same.

Hereinafter, the present disclosure will be described in detail.

The deslorelin sustained-release microsphere is prepared by using two or more polymers selected from the group consisting of poly(lactide-co-glycolide) and polylactide polymers having a lactide-to-glycolide ratio of 50:50 to 100:0 and an intrinsic viscosity of 0.16 to 1.20 dL/g.

The deslorelin microsphere of the present disclosure is a release-controlling agent, and preferably uses two or more polymers selected from the group consisting of poly(lactide-co-glycolide) and polylactide polymers having a lactide-to-glycolide ratio of 50:50 to 100:0 and an intrinsic viscosity of 0.16 to 1.20 dL/g. The intrinsic viscosity of the poly(lactide-co-glycolide) or polylactide used in the present disclosure refers to an intrinsic viscosity measured at a concentration of 0.1% (w/v) in chloroform at 25° C. using Ubbelohde viscometer. When the intrinsic viscosity of the poly(lactide-co-glycolide) or polylactide is less than 0.16 dL/g, the molecular weight of the polymer is not sufficient and thus, it is difficult to exhibit the sustained-release effect of the deslorelin drug. When the intrinsic viscosity exceeds 1.20 dL/g, it may exhibits the effect of excessively delaying the release of the deslorelin drug. Further, when preparing the microsphere using a polymer having a high intrinsic viscosity, there is a problem in that an excessive amount of a production solvent must be used due to the high viscosity of the polymer, and it is difficult to prepare a reproducible microsphere. Examples of commercially available polymers having the above-mentioned properties include RG502H, RG503H, RG504H, RG502, RG503, RG504, RG653H, RG752H, RG752S, RG755S, RG750S, R202H, R203H, R205H, R202S, R203S, R205S, R206S, and R207S (Resomer series available from Evonik), and PDL 02A, PDL 02, PDL 04, PDL 05, PDLG 7502A, PDLG 7502, PDLG 7507, PDLG 5002A, PDLG 5002, PDLG 5004A and PDLG 5004 (available from Corbion Purac), and the like.

The content of deslorelin in the sustained-release microsphere containing deslorelin according to the present disclosure is preferably 5% to 25% by weight based on the total weight of the deslorelin microsphere. The content of deslorelin is more preferably 10% to 20% by weight. When the content of deslorelin in the microsphere is less than 5% by weight, the amount of the polymer used is too high, which may reduce the bioavailability of deslorelin, and when the content of deslorelin is higher than 25% by weight, there is a problem that the initial release of deslorelin increases, which is not preferable.

It is preferable that the microspheres containing deslorelin according to the present disclosure have a uniform particle distribution chart with an average particle size of 10 µm to 100 µm. The term "average particle size" as used herein refers to a median diameter as the particle size corresponding to 50% of the volume % in the particle size distribution curve, and is represented by D50 or D(v, 0.5).

When the average particle size of the microsphere containing deslorelin is less than 10 µm, the release of the deslorelin drug from the microsphere is too rapid, which is not preferable. When the average particle size is greater than 100 µm, an injection needle becomes too thicker when administered in an animal, which causes pain during injection, or the drug may leak to the injection site after injection, which is not preferable.

Preferably, the microsphere containing deslorelin of the present disclosure has a uniform particle distribution. The microsphere containing deslorelin having a uniform particle distribution has less deviation during injection than a non-uniform microsphere and can be administered in a more accurate amount. Preferably, the size distribution or span value of the microsphere containing deslorelin of the present disclosure is 1.2 or less. More preferably, the size distribution is 1.0 or less. The size distribution or span value as used herein is an index indicating the uniformity of the particle size of the microsphere, and means a value determined by the formula of span value=(Dv0.9−Dv0.1)/Dv0.5. Here, Dv0.1 means a particle size corresponding to 10% of the volume % in the particle size distribution curve of the microsphere, Dv0.5 refers to a particle size corresponding to 50% of the volume % in the particle size distribution curve of the microsphere, and Dv0.9 means a particle size corresponding to 90% of the volume % in the particle size distribution curve of the microsphere.

The sustained-release microspheres containing deslorelin of the present disclosure are administered to an animal via subcutaneous or intramuscular route, and if no release is desired any more after a certain period of time, since there is no way to recover it except for surgical operation, it is desirable that most of the drugs be released for 6 months in the sustained-release microspheres containing deslorelin of the present disclosure. Therefore, the sustained-release microsphere containing deslorelin of the present disclosure is not particularly limited in such a release aspect, but when administered in vivo, it is desirable that at least 85% of the drug is released within 6 months.

In a specific embodiment, it was confirmed that in the sustained-release microspheres containing deslorelin according to the present disclosure, preferably, 10% or more of the drug is released within 1 month after administration and 85% or more of the drug is released within 6 months after administration, more preferably, 15% or more of the drug is released within 1 month after administration, 40% to 80% within 3 months after administration, and 85% or more within 6 months after administration, and most preferably, 15% to 70% of the drug is released within 1 month after administration of microsphere, 40% to 80% of the drug is released within 3 months after administration, and 90% or more of the drug is released within 6 months after administration.

Hereinafter, a method for preparing the sustained-release microsphere injection formulation containing deslorelin of the present disclosure will be described in detail.

The sustained-release microsphere injection formulation containing deslorelin according to the present disclosure may be prepared, for example, using the "solvent extraction/evaporation method", without being limited thereto.

As a specific example of the method for preparing a sustained-release microsphere containing deslorelin according to the present disclosure, such preparation method includes the steps of: (a) dissolving deslorelin and two or more polymers selected from the group consisting of poly (lactide-co-glycolide) and polylactide polymers in a mixed organic solvent to prepare a deslorelin-polymer solution (dispersed phase), (b) adding the deslorelin-polymer solution prepared in step (a) to an aqueous solution phase (continuous phase) containing a surfactant to prepare a dispersed phase in an emulsion state, (c) extracting and the organic solvent from the dispersed phase in the emulsion state phase prepared in step (b) into a continuous phase and evaporating the organic solvent to form a microsphere and (d) recovering the microsphere from the continuous phase of step (c) to prepare a deslorelin microsphere.

It is preferable that the sustained-release microsphere containing deslorelin according to the present disclosure uses two or more poly(lactide-co-glycolide) or polylactide polymers, in order to sufficiently release the drug at initial stage for rapid drug effect and release the drug at a constant concentration for 6 months.

The sustained-release microsphere containing deslorelin according to the present disclosure can be prepared by a process in which in step (a), deslorelin and two or more polymers selected from the group consisting of poly(lactide-co-glycolide) and polylactide polymers are simultaneously dissolved in a mixed organic solvent to prepare a deslorelin sustained-release microsphere containing two or more polymers.

Further, the sustained-release microsphere containing deslorelin according to the present disclosure can be prepared by mixing two or more different deslorelin-containing microspheres including different polymers prepared through the steps (a) to (d) using two or more different poly(lactide-co-glycolide) or polylactide polymers.

In a specific embodiment, as described above, the method of selecting two or more different polymers from the group consisting of poly(lactide-co-glycolide) and polylactide, respectively, and then preparing two or more different deslorelin-containing microspheres using these polymers may include the following steps.

Preparing two or more different preliminary microspheres using two or more different polymers selected from the group consisting of poly(lactide-co-glycolide) or polylactide polymer and deslorelin; and mixing the two or more different preliminary microspheres, wherein the step of preparing the two or more different preliminary microspheres may include the following steps:

(a) dissolving deslorelin and poly(lactide-co-glycolide) or polylactide polymer in a mixed organic solvent to prepare a deslorelin-polymer solution (dispersed phase);

(b) adding the deslorelin-polymer solution prepared in step (a) to an aqueous solution phase (continuous phase) containing a surfactant to prepare a dispersed phase in an emulsion state;

(c) extracting the organic solvent from the dispersed phase in the emulsion state prepared in step (b) into a continuous phase and evaporating the organic solvent to form a microsphere; and (d) recovering the microsphere from the continuous phase of step (c) to prepare the preliminary microsphere.

In a specific embodiment, the steps of preparing the two or more different preliminary microspheres may be performed sequentially or simultaneously.

In step (a), the intrinsic viscosity of poly(lactide-co-glycolide) or polylactide is preferably in the range of 0.16 to 1.2 dL/g.

The mixed solvent used for dissolving deslorelin and two or more polymers selected from the group consisting of poly(lactide-co-glycolide) and polylactide in step (a) preferably use at least 50% (v/v) or more of a solvent with properties that are immiscible with water. By utilizing the properties of the organic solvents that are immiscible with water, the dispersed phase can be homogeneously mixed in the continuous phase containing a surfactant in step (b) described later, thereby forming an emulsion. The type of the mixed solvent that dissolves such deslorelin and poly(lactide-co-glycolide) or polylactide is not particularly limited. Preferably, a mixed solvent of two or more solvents selected from the group consisting of dichloromethane, chloroform, ethyl acetate, methyl ethyl ketone, acetone, acetonitrile, dimethyl sulfoxide, dimethylformamide, N-methylpyrrolidone, acetic acid, methyl alcohol, ethyl alcohol, propyl alcohol and benzyl alcohol, and more preferably, one or more mixed solvents selected from one solvent selected from dichloromethane and ethyl acetate, and dimethyl sulfoxide, N-methylpyrrolidone and methyl alcohol can be used.

In step (b), the method of homogeneously mixing the deslorelin-polymer solution and the continuous phase containing the surfactant is not particularly limited, and the mixing can be performed using a high-speed stirrer, an in-line mixer, a membrane emulsification method, a microfluidic emulsification method, or the like. When an emulsion is formed using a high-speed stirrer or an in-line mixer, since it is difficult to obtain a uniform emulsion, it is preferable to additionally perform a sieving step or the like between steps (c) and (d) described later. When an emulsion is formed using a membrane emulsification method or a microfluidic emulsification method, an emulsion having a uniform size can be obtained, and thus an additional sieving step or the like is not required between steps (c) and (d) described later, which is more preferable.

The type of surfactant used in step (b) is not particularly limited, and the surfactant can be used without limitation as long as it can help the deslorelin-polymer solution to form a stable droplet dispersed phase within the continuous phase. Preferably, the surfactant can be selected from the group consisting of methylcellulose, polyvinylpyrrolidone, carboxymethylcellulose, lecithin, gelatin, polyvinyl alcohol, polyoxyethylene sorbitan fatty acid ester, polyoxyethylene castor oil derivatives, and mixtures thereof. Most preferably, polyvinyl alcohol may be used.

In step (b), the content of the surfactant in the continuous phase containing the surfactant may be 0.01 w/v % to 20 w/v %, preferably 0.1 w/v % to 5 w/v % based on the total volume of the continuous phase containing the surfactant. When the content of the surfactant is less than 0.01 w/v %, a dispersed phase or emulsion in the form of droplets may not be formed in the continuous phase, and when the content of the surfactant exceeds 20 w/v %, it may be difficult to remove the surfactant after fine particles are formed in the continuous phase due to an excessive surfactant.

The continuous phase used in step (b) may use water, and in order to regulate the extraction rate of the organic solvent from the dispersed phase in an emulsion state, water containing a part of one or more selected from the group consisting of methyl alcohol, ethyl alcohol, propyl alcohol and ethyl acetate can be used.

In step (c), when the emulsion containing a dispersed phase in the form of droplets and a continuous phase containing a surfactant is maintained or stirred at a temperature below the boiling point of the organic solvent for a certain period of time, for example, 2 to 48 hours, the organic solvent may be extracted into a continuous phase from a deslorelin-polymer solution in the form of a droplet which is a dispersed phase. A part of the organic solvent extracted into the continuous phase can be evaporated from the surface of the continuous phase. As the organic solvent is extracted and evaporated from the deslorelin-polymer solution in the form of droplets, the dispersed phase in the form of droplets can be solidified to form microspheres.

In step (c), in order to efficiently remove the organic solvent, the temperature of the continuous phase may be heated for a certain period of time.

In step (d), the method of recovering the microspheres containing deslorelin may be performed using several known techniques, and for example, a method such as filtration or centrifugation can be used.

Between steps (c) and (d), the residual surfactant may be removed through filtration and washing, and then the filtration may be performed again to recover the microspheres.

The washing step for removing the residual surfactant can be generally performed using water, and the washing step may be repeated several times.

Further, as described above, when the emulsion is formed using a high-speed stirrer and an in-line mixer in step (b), a uniform microsphere can be obtained by additionally using a seiving step between steps (c) and (d). A sieving step can be performed using a known technique, and microspheres of small particles and large particles can be filtered using a sieve membrane having different sizes to obtain microspheres of uniform size.

In the preparation method of the present disclosure, after step (d) or after the filtration and washing step, the obtained microspheres are dried using a conventional drying method to finally obtain the dried microspheres.

According to the preparation method of the present disclosure, it is possible to prepare a sustained-release microsphere injection formulation containing homogeneous particles of deslorelin which has good administrability and enables, with a single administration, a deslorelin drug to be maintained at an effective concentration for 6 months without rapid temporary release into the blood of an animal.

Advantageous Effects

The deslorelin-containing sustained-release microsphere injection formulation according to the present disclosure has good administrability and enables, with a single administration, a deslorelin drug to be maintained at an effective concentration for 6 months or more without rapid temporary release into the blood of an animal.

DETAILED DESCRIPTION OF THE EMBODIMENTS

Hereinafter, the present disclosure will be described in more detail by way of examples. However, these examples are for illustrative purposes only, and the scope of the present disclosure is not limited thereto.

Comparative Example

Comparative Example 1: Preparation 1 of a Sustained-Release Microsphere Injection Formulation Containing Deslorelin Prepared Using a Single Polymer The dispersed phase was prepared by mixing 9 g of biocompatible polymer Resomer R203H (manufacturer: Evonik, Germany) and 1 g of deslorelin acetate (manufacturer: Chengdu Kaijie Biopharm Co., Ltd, China) with 32.14 g of dichloromethane (manufacturer: J. T. Baker, USA) and 9.59 ml of N-methylpyrrolidone (manufacturer: JUNSEI, Japan). The dispersed phase was stirred for at least 30 minutes and sufficiently dissolved before use. As the continuous phase, a 1 wt % polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 1-1: Preparation 2 of a Sustained-Release Microsphere Injection Formulation Containing Deslorelin Prepared Using a Single Polymer The dispersed phase was prepared by mixing 8.5 g of biocompatible polymer Resomer R203H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 1-2: Preparation 3 of a Sustained-Release Microsphere Injection Formulation Containing Deslorelin Prepared Using a Single Polymer The dispersed phase was prepared by mixing 2.4 g of biocompatible polymer Resomer R203H (manufacturer: Evonik, Germany) and 0.6 g of deslorelin acetate (manufacturer: Chengdu Kaijie Biopharm Co., Ltd, China) with 8.57 g of dichloromethane (manufacturer: J. T. Baker, USA) and 2.56 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 1-3: Preparation 4 of a Sustained-Release Microsphere Injection Formulation Containing Deslorelin Prepared Using a Single Polymer The dispersed phase was prepared by mixing 7.0 g of biocompatible polymer Resomer R203H (manufacturer: Evonik, Germany) and 3.0 g of deslorelin acetate (manufacturer: Chengdu Kaijie Biopharm Co., Ltd, China) with 25.0 g of dichloromethane (manufacturer: J. T. Baker, USA) and 7.46 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 2: Preparation 5 of a Sustained-Release Microsphere Injection Formulation Containing Deslorelin Prepared Using a Single Polymer The dispersed phase was prepared by mixing 8.5 g of biocompatible polymer Resomer R202H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 3: Preparation 6 of a Sustained-Release Microsphere Injection Formulation Containing Deslorelin Prepared Using a Single Polymer The dispersed phase was prepared by mixing 8.5 g of biocompatible polymer Resomer R205S (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 4: Preparation 7 of a Sustained-Release Microsphere Injection Formulation Containing Deslorelin Prepared Using a Single Polymer The dispersed phase was prepared by mixing 9.0 g of biocompatible polymer Resomer RG752H (manufacturer: Evonik, Germany) and 1.0 g of deslorelin acetate (manufacturer: Chengdu Kaijie Biopharm Co., Ltd, China) with 32.14 g of dichloromethane (manufacturer: J. T. Baker, USA) and 9.59 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 5: Preparation 8 of a Sustained-Release Microsphere Injection Formulation Containing Deslorelin Prepared Using a Single Polymer The dispersed phase was prepared by mixing 2.55 g of biocompatible polymer Resomer RG753H (manufacturer: Evonik, Germany) and 0.45 g of deslorelin acetate (manufacturer: Chengdu Kaijie Biopharm Co., Ltd, China) with 9.11 g of dichloromethane (manufacturer: J. T. Baker, USA) and 2.72 ml of methylalcohol (manufacturer: Tedia Company, USA). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 30 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 6: Preparation 9 of a Sustained-Release Microsphere Injection Formulation Containing Deslorelin Prepared Using a Single Polymer The dispersed phase was prepared by mixing 8.5 g of biocompatible polymer Resomer RG653H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 6-1: Preparation 10 of a Sustained-Release Microsphere Injection Formulation Containing Deslorelin Prepared Using a Single Polymer The dispersed phase was prepared by mixing 4.5 g of biocompatible polymer Resomer RG653H (manufacturer: Evonik, Germany) and 0.5 g of deslorelin acetate (manufacturer: Chengdu Kaijie Biopharm Co., Ltd, China) with 16.07 g of dichloromethane (manufacturer: J. T. Baker, USA) and 4.8 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 7: Preparation 11 of a Sustained-Release Microsphere Injection Formulation Containing Deslorelin Prepared Using a Single Polymer The dispersed phase was prepared by mixing 8.5 g of biocompatible polymer Resomer RG503H (manufacturer: Evonik, Germany) and 1.5 g of deslorelin acetate (manufacturer: Chengdu Kaijie Biopharm Co., Ltd, China) with 30.06 g of dichloromethane (manufacturer: J. T. Baker, USA) and 9.06 ml of methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 8: Preparation 12 of a Sustained-Release Microsphere Injection Formulation Containing Deslorelin Prepared Using a Single Polymer The dispersed phase was prepared by mixing 8.5 g of biocompatible polymer Resomer RG858S (manufacturer: Evonik, Germany) and 1.5 g of deslorelin acetate (manufacturer: Chengdu Kaijie Biopharm Co., Ltd, China) with 60.71 g of dichloromethane (manufacturer: J. T. Baker, USA) and 18.12 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 9: Preparation 1 of a Sustained-Release Microsphere Injection Formulation Containing Deslorelin Prepared Using Two Types of Polymers In order to prepare a sustained-release microsphere injection formulation having an average particle size of 100 µm or more using two types of polymers with a high-speed stirrer, a sustained-release microsphere injection formulation containing deslorelin was prepared according to the following method. The dispersed phase was prepared by mixing 1.91 g of biocompatible polymer Resomer R203H (manufacturer: Evonik, Germany), 0.64 g of Resomer RG752H (manufacturer: Evonik, Germany) and 0.45 g of deslorelin acetate (manufacturer: Chengdu Kaijie Biopharm Co., Ltd, China) with 9.11 g of dichloromethane (manufacturer: J. T. Baker, USA) and 2.72 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was added to the continuous phase and stirred at 1000 rpm using a high-speed stirrer to form an emulsion, which was stirred at 40° C. for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 10: Preparation 2 of a Sustained-Release Microsphere Injection Formulation Containing Deslorelin Prepared Using Two Types of Polymers In order to prepare a sustained-release microsphere injection formulation having an average particle size of 100 µm or more using two types of polymers with a high-speed stirrer, a sustained-release microsphere injection formulation containing deslorelin was prepared according to the following method. In order to prepare a sustained-release microsphere injection formulation within an average particle size of 100 µm, the RPM of the high-speed stirrer was relatively increased and the injection formulation was prepared as follows. The dispersed phase was prepared by mixing 1.91 g of biocompatible polymer Resomer R203H (manufacturer: Evonik, Germany), 0.64 g of Resomer RG752H (manufacturer: Evonik, Germany) and 0.45 g of deslorelin acetate (manufacturer: Chengdu Kaijie Biopharm Co., Ltd, China) with 9.11 g of dichloromethane (manufacturer: J. T. Baker, USA) and 2.72 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was added to the continuous phase and stirred at 1000 rpm using a high-speed stirrer to form an emulsion, which was stirred at 40° C. for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 11: Preparation 3 of a Sustained-Release Microsphere Injection Formulation Containing Deslorelin Prepared Using Two Types of Polymers In order to prepare a sustained-release microsphere injection formulation using two types of polymers, wherein the drug introduced for preparing the formulation was used in an amount of 40 wt. % based on the total solid content, and the final content of deslorelin in the sustained-release microsphere injection formulation was as high as 27.3 wt. %, a sustained-release microsphere injection formulation was prepared according to the following method. The dispersed phase was prepared by mixing 1.35 g of biocompatible polymer Resomer R203H (manufacturer: Evonik, Germany), 0.45 g of Resomer RG752H (manufacturer: Evonik, Germany) and 1.2 g of deslorelin acetate (manufacturer: Chengdu Kaijie Biopharm Co., Ltd, China) with 6.43 g of dichloromethane (manufacturer: J. T. Baker, USA) and 1.92 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 50 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 12: Preparation 4 of a Sustained-Release Microsphere Injection Formulation Containing Deslorelin Prepared Using Two Types of Polymers In order to prepare a sustained-release microsphere injection formulation using two types of polymers, wherein the drug introduced for preparing the formulation was used in an amount of 5 wt. % based on the total solid content, and the final content of deslorelin in the sustained-release microsphere injection formulation was as low as 4.2 wt. %, a sustained-release microsphere injection formulation was prepared according to the following method. The dispersed phase was prepared by mixing 2.14 g of biocompatible polymer Resomer R203H (manufacturer: Evonik, Germany), 0.71 g of Resomer RG752H (manufacturer: Evonik, Germany) and 0.15 g of deslorelin acetate (manufacturer: Chengdu Kaijie Biopharm Co., Ltd, China) with 10.18 g of dichloromethane (manufacturer: J. T. Baker, USA) and 3.04 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Comparative Example 13: Preparation 5 of a Sustained-Release Microsphere Injection Formulation Containing Deslorelin Prepared Using Two Types of Polymers In order to prepare a sustained-release microsphere injection formulation using two types of polymers, provided that a ratio of PLA to PLGA (PLA:PLGA) was set to 1:3, a sustained-release microsphere injection formulation was prepared according to the following method. The dispersed phase was prepared by mixing 1.06 g of biocompatible polymer Resomer R203H (manufacturer: Evonik, Germany), 3.19 g of Resomer RG752H (manufacturer: Evonik, Germany) and 0.75 g of deslorelin acetate (manufacturer: Chengdu Kaijie Biopharm Co., Ltd, China) with 15.18 g of dichloromethane (manufacturer: J. T. Baker, USA) and 4.53 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

EXAMPLE

In Examples, when preparing a sustained-release microsphere injection formulation containing deslorelin, two or more types of polymers were used, or two or more formulations prepared using a single polymer were mixed.

Example 1: Preparation 1 of a Sustained-Release Microsphere Injection Formulation Containing Deslorelin Prepared Using Two Types of Polymers The dispersed phase was prepared by mixing 6.375 g of biocompatible polymer Resomer R203H (manufacturer:

Evonik, Germany), 2.125 g of Resomer RG858S (manufacturer: Evonik, Germany) and 1.5 g of deslorelin acetate (manufacturer: Chengdu Kaijie Biopharm Co., Ltd, China) with 37.95 g of dichloromethane (manufacturer: J. T. Baker, USA) and 11.33 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 2: Preparation 2 of a Sustained-Release Microsphere Injection Formulation Containing Deslorelin Prepared Using Two Types of Polymers The dispersed phase was prepared by mixing 7.65 g of biocompatible polymer Resomer R203H (manufacturer: Evonik, Germany), 0.85 g of Resomer RG752H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 3: Preparation 3 of a Sustained-Release Microsphere Injection Formulation Containing Deslorelin Prepared Using Two Types of Polymers The dispersed phase was prepared by mixing 6.375 g of biocompatible polymer Resomer R203H (manufacturer: Evonik, Germany), 2.125 g of Resomer RG753H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 4: Preparation 4 of a Sustained-Release Microsphere Injection Formulation Containing Deslorelin Prepared Using Two Types of Polymers The dispersed phase was prepared by mixing 4.25 g of biocompatible polymer Resomer R203H (manufacturer: Evonik, Germany), 4.25 g of Resomer RG752H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of methylalcohol (manufacturer: TEDIA Company, USA). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 5: Preparation 5 of a Sustained-Release Microsphere Injection Formulation Containing Deslorelin Prepared Using Two Types of Polymers The dispersed phase was prepared by mixing 6.375 g of biocompatible polymer Resomer R203H (manufacturer: Evonik, Germany), 2.125 g of Resomer RG653H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 6: Preparation 6 of a Sustained-Release Microsphere Injection Formulation Containing Deslorelin Prepared Using Two Types of Polymers The dispersed phase was prepared by mixing 6.375 g of biocompatible polymer Resomer R203H (manufacturer:

Evonik, Germany), 2.125 g of Resomer RG503H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 14.73 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 50 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 7: Preparation 7 of a Sustained-Release Microsphere Injection Formulation Containing Deslorelin Prepared Using Two Types of Polymers The dispersed phase was prepared by mixing 6.375 g of biocompatible polymer Resomer R202H (manufacturer: Evonik, Germany), 2.125 g of Resomer RG858S (manufacturer: Evonik, Germany) and 1.5 g of deslorelin acetate (manufacturer: Chengdu Kaijie Biopharm Co., Ltd, China) with 37.95 g of dichloromethane (manufacturer: J. T. Baker, USA) and 11.33 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 8: Preparation 8 of a Sustained-Release Microsphere Injection Formulation Containing Deslorelin Prepared Using Two Types of Polymers The dispersed phase was prepared by mixing 6.375 g of biocompatible polymer Resomer R202H (manufacturer: Evonik, Germany), 2.125 g of Resomer RG752H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of methylalcohol (manufacturer: TEDIA Company, USA). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 9: Preparation 9 of a Sustained-Release Microsphere Injection Formulation Containing Deslorelin Prepared Using Two Types of Polymers The dispersed phase was prepared by mixing 6.375 g of biocompatible polymer Resomer R202H (manufacturer: Evonik, Germany), 2.125 g of Resomer RG653H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 20 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 9-1: Preparation 9-1 of a Sustained-Release Microsphere Injection Formulation Containing Deslorelin Prepared Using Two Types of Polymers The dispersed phase was prepared by mixing 2.775 g of biocompatible polymer Resomer R202H (manufacturer: Evonik, Germany), 1.85 g of Resomer RG653H (manufacturer: Evonik, Germany) and 0.375 g of deslorelin acetate (manufacturer: Chengdu Kaijie Biopharm Co., Ltd, China) with 16.52 g of dichloromethane (manufacturer: J. T. Baker, USA) and 4.93 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 5 µm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 9-2: Preparation 9-2 of a Sustained-Release Microsphere Injection Formulation Containing Deslorelin Prepared Using Two Types of Polymers The dispersed phase was prepared by mixing 2.25 g of biocompatible polymer Resomer R202H (manufacturer:

Evonik, Germany), 1.5 g of Resomer RG653H (manufacturer: Evonik, Germany) and 1.25 g of deslorelin acetate (manufacturer: Chengdu Kaijie Biopharm Co., Ltd, China) with 13.39 g of dichloromethane (manufacturer: J. T. Baker, USA) and 4.00 ml of dimethyl sulfoxide (manufacturer: Samchun Pure Chemical Co., Ktd., South Korea). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 5 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 10: Preparation 10 of a Sustained-Release Microsphere Injection Formulation Containing Deslorelin Prepared Using Two Types of Polymers The dispersed phase was prepared by mixing 6.375 g of biocompatible polymer Resomer R202H (manufacturer: Evonik, Germany), 2.125 g of Resomer RG503H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 40 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Example 11: Preparation 11 of a Sustained-Release Microsphere Injection Formulation Containing Deslorelin Prepared Using Two Types of Polymers The dispersed phase was prepared by mixing 4.25 g of biocompatible polymer Resomer R203H (manufacturer: Evonik, Germany), 2.125 g of Resomer RG752H (manufacturer: Evonik, Germany), 2.125 g of Resomer RG503H (manufacturer: Evonik, Germany) and 1.5 g of deslorelin acetate (manufacturer: Chengdu Kaijie Biopharm Co., Ltd, China) with 30.36 g of dichloromethane (manufacturer: J. T. Baker, USA) and 9.06 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was connected and injected to an emulsififcation apparatus equipped with a porous membrane (pore size: 40 μm), and at the same time, the prepared dispersed phase was injected to form an emulsion. The emulsion was stirred at 40° C. at 200 rpm for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol, and then lyophilized, thereby obtaining a microsphere containing deslorelin.

Examples 12-22. Preparation of a Formulation Containing Two or More Types of Microspheres Containing Different Polymers The sustained-release microsphere formulations containing deslorelin prepared in Comparative Example were mixed based on the polymer and ratio as shown in Table 1 below, and used as Examples 12-22.

TABLE 1

| Category | Microsphere 1 | Microsphere 2 | Microsphere 3 | Mixing ratio | | |
|---|---|---|---|---|---|---|
| Example 12 | Comparative Example 1-3 | Comparative Example 8 | — | 3 | 1 | — |
| Example 13 | Comparative Example 1-3 | Comparative Example 4 | — | 9 | 1 | — |
| Example 14 | Comparative Example 1-3 | Comparative Example 5 | — | 3 | 1 | — |
| Example 15 | Comparative Example 1-3 | Comparative Example 4 | — | 1 | 1 | — |
| Example 16 | Comparative Example 1-3 | Comparative Example 6 | — | 3 | 1 | — |
| Example 17 | Comparative Example 1-3 | Comparative Example 7 | — | 3 | 1 | — |
| Example 18 | Comparative Example2 | Comparative Example 8 | — | 3 | 1 | — |
| Example 19 | Comparative Example2 | Comparative Example 4 | — | 3 | 1 | — |
| Example 20 | Comparative Example2 | Comparative Example 6 | — | 3 | 1 | — |
| Example 21 | Comparative Example2 | Comparative Example 7 | — | 3 | 1 | — |
| Example 22 | Comparative Example 1-3 | Comparative Example4 | Comparative Example 7 | 2 | 1 | 1 |

Example 23: Preparation 12 of a Sustained-Release Microsphere Injection Formulation Containing Deslorelin Prepared Using Two Types of Polymers The dispersed phase was prepared by mixing 4.25 g of biocompatible polymer Resomer R207S (manufacturer: Evonik, Germany), 4.25 g of Resomer RG752H (manufacturer: Evonik, Germany) and 1.5 g of deslorelin acetate (manufacturer: Chengdu Kaijie Biopharm Co., Ltd, China) with 42.5 g of dichloromethane (manufacturer: J. T. Baker, USA) and 12.69 ml of N-methylpyrrolidone (manufacturer: JUNSEI, Japan). The dispersed phase was stirred for at least 30 minutes and sufficiently dissolved before use. As the continuous phase, a 1% polyvinyl alcohol aqueous solution (viscosity: 4.8 to 5.8 mPa·s) was used. The dispersed phase was added to the continuous phase and then stirred at 2000 rpm using a high-speed stirrer to form an emulsion, which was stirred at 40° C. for 3 hours to remove the organic solvent. When the removal of the organic solvent was completed, the temperature of the microsphere suspension was set to 25° C., and the microsphere suspension was repeatedly washed with distilled water several times to remove residual polyvinyl alcohol. Then, particles larger than 150 pm and smaller than 25 μm using 100 mesh (150

μm) and 500 mesh (25 μm) sieves were removed, and then lyophilized, thereby obtaining a microsphere containing deslorelin.

Experimental Example

Experimental Example 1. Measurement of Deslorelin Content in Microsphere

In order to measure the amount of encapsulation of deslorelin in the microspheres prepared in Comparative Examples 1-13 and 1-11, 2 mg of microspheres were completely dissolved in acetonitrile, and then diluted with a mobile phase. 20 μL of the diluted solution was injected into HPLC and measured at a detection wavelength of 280 nm. The column used in this measurement was Gemini C18 5 μm, 4.6×150 mm, and the mobile phase (A) 0.1% TFA aqueous solution and (B) acetonitrile containing 0.1% TFA were used in gradient mode with (B) being 20-50%.

The content of deslorelin in the microspheres prepared in Comparative Example is shown in Table 2 below.

TABLE 2

Deslorelin content of the sustained-release microsphere injection formulations containing deslorelin (Comparative Example)

| Sample | Drug content (%) |
|---|---|
| Comparative Example 1 | 9.7 |
| Comparative Example 1-1 | 12.2 |
| Comparative Example 1-2 | 16.2 |
| Comparative Example 1-3 | 22.0 |
| Comparative Example 2 | 12.8 |
| Comparative Example 3 | 10.2 |
| Comparative Example 4 | 7.6 |
| Comparative Example 5 | 13.4 |
| Comparative Example 6 | 15.1 |
| Comparative Example 6-1 | 8.8 |
| Comparative Example 7 | 13.3 |
| Comparative Example 8 | 10.6 |
| Comparative Example 9 | 12.6 |
| Comparative Example 10 | 12.1 |
| Comparative Example 11 | 27.3 |
| Comparative Example 12 | 4.2 |
| Comparative Example 13 | 11.5 |

In Comparative Examples 1 to 8, a formulation was prepared using a single polymer, wherein the preparation was performed by changing the type of polymer and the target content of drug. Based on the results confirmed in Table 2, it was confirmed that there was a difference in the encapsulation rate of the drug depending on the type of polymer. In general, when the terminal group of the polymer used for preparing the formulation is an ester group, it was confirmed that the drug encapsulation rate tends to be relatively low. In Comparative Examples 9 to 10, examples in which the formulations were prepared using a high-speed stirrer, it was confirmed that the drug content was not significantly affected even if the preparation method was changed. Further, Comparative Examples 11 to 12 are formulations prepared by changing the amount of deslorelin compared to the total solid content added in the preparation of microspheres, and it was confirmed that the content of the final drug was significantly varied depending on the amount of the drug, and it was confirmed that the higher the drug input ratio, the lower the encapsulation efficiency. Comparative Example 13 is an example in which when preparing a formulation using two types of polymers, the mixing ratio is PLA: PLGA=1:3, and it was confirmed that there was no difference in the drug encapsulation efficiency depending on the composition ratio of the polymer.

The content of deslorelin in the microspheres of Examples 1 to 23 is shown in Table 3 below.

TABLE 3

Deslorelin content of sustained-release microsphere injection formulations containing deslorelin (Example)

| Sample | Drug content (%) |
|---|---|
| Example 1 | 12.20 |
| Example 2 | 12.60 |
| Example 3 | 12.00 |
| Example 4 | 12.40 |
| Example 5 | 13.20 |
| Example 6 | 12.80 |
| Example 7 | 12.20 |
| Example 8 | 12.50 |
| Example 9 | 13.20 |
| Example 9-1 | 5.10 |
| Example 9-2 | 23.30 |
| Example 10 | 12.90 |
| Example 11 | 12.80 |
| Example 12 | 11.80 |
| Example 13 | 11.74 |
| Example 14 | 11.05 |
| Example 15 | 9.90 |
| Example 16 | 12.93 |
| Example 17 | 12.48 |
| Example 18 | 12.25 |
| Example 19 | 11.50 |
| Example 20 | 13.38 |
| Example 21 | 12.93 |
| Example 22 | 11.63 |
| Example 23 | 10.70 |

Experimental Example 2. Morphological Analysis of Sustained-Release Microsphere Injection Formulation Containing Deslorelin Through Electron Microscope To analyze the morphological properties of microspheres, a scanning electron microscope observation was performed. The microspheres were coated with platinum using Ion-Coater (COXEM, Korea), and then the morphological properties of the microspheres were observed at an acceleration voltage of 15 kV with a scanning electron microscope (COXEM EM-30, Korea), and the results are shown in FIG. 1.

Figure 1:
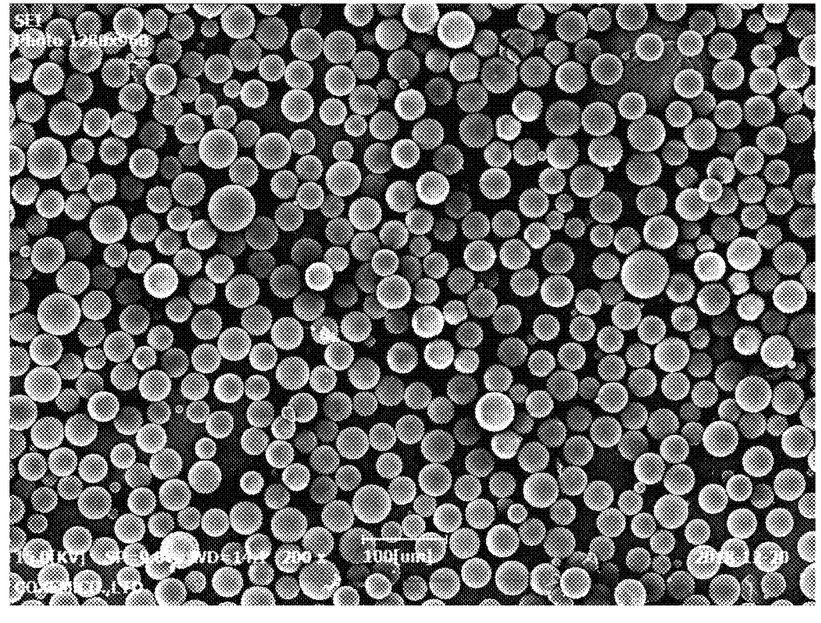
FIG. 1 is a photograph of a sustained-release microsphere injection formulation containing deslorelin prepared in Example 3 when observed with an electron microscope.

FIG. 1 is a photograph of a sustained-release microsphere injection formulation containing deslorelin prepared in Example 3 when observed with an electron microscope. According to FIG. 1, it was confirmed that microspheres having a very uniform particle size were prepared.

Experimental Example 3. Particle Size Analysis of Sustained-Release Microsphere Injection Formulation Containing Deslorelin Using a Laser Diffraction Method To quantitatively measure the average particle size, distribution and uniformity of the microspheres, the experiment was performed using a laser diffraction method. The microspheres prepared in Comparative Examples and Examples were mixed with ultrapure water containing a surfactant, mixed with a vortex mixer for 20 seconds, and then placed in an ultrasonic generator and dispersed. This solution was placed in a particle size analyzer (Microtrac Bluewave, Japan) and the particle size was measured.

As an index of particle size uniformity, the span value was determined by the following Equation 1.

$$\text{Span Value} = (Dv0.9 - Dv0.1)/Dv0.5 \quad [\text{Equation 1}]$$

The particle size measurement results of the sustained-release formulation containing deslorelin prepared in Comparative Examples are shown in Table 4 below.

TABLE 4

Particle size of sustained-release microsphere injection formulation containing deslorelin (Comparative Example)

| Sample | Dv0.5(μm) | Span value |
|---|---|---|
| Comparative Example 1 | 33.16 | 0.78 |
| Comparative Example 1-1 | 33.32 | 0.75 |
| Comparative Example 1-2 | 35.76 | 0.76 |
| Comparative Example 1-3 | 38.22 | 0.97 |
| Comparative Example 2 | 35.52 | 0.63 |
| Comparative Example 3 | 33.05 | 0.60 |
| Comparative Example 4 | 28.17 | 0.59 |
| Comparative Example 5 | 45.23 | 0.63 |
| Comparative Example 6 | 40.35 | 1.66 |
| Comparative Example 6-1 | 33.05 | 0.60 |
| Comparative Example 7 | 37.22 | 1.04 |
| Comparative Example 8 | 31.78 | 0.63 |
| Comparative Example 9 | 114.72 | 0.53 |
| Comparative Example 10 | 98.21 | 0.67 |
| Comparative Example 11 | 63.86 | 1.33 |
| Comparative Example 12 | 38.22 | 0.97 |
| Comparative Example 13 | 33.23 | 0.68 |

The particle size measurement results of the sustained-release microsphere formulation containing deslorelin prepared in Example are shown in Table 5 below.

TABLE 5

Particle size of sustained-release microsphere injection formulation containing deslorelin (Example)

| Sample | Dv0.5(μm) | Span value |
|---|---|---|
| Example 1 | 36.23 | 0.73 |
| Example 2 | 38.60 | 0.82 |
| Example 3 | 38.26 | 0.81 |
| Example 4 | 46.39 | 1.03 |
| Example 5 | 36.83 | 0.63 |
| Example 6 | 65.85 | 0.76 |
| Example 7 | 38.04 | 0.64 |
| Example 8 | 38.39 | 0.63 |
| Example 9 | 40.40 | 0.92 |
| Example 9-1 | 15.95 | 0.98 |
| Example 9-2 | 19.20 | 1.02 |
| Example 10 | 50.37 | 0.93 |
| Example 11 | 53.43 | 1.10 |
| Example 12 | 32.94 | 0.72 |
| Example 13 | 32.81 | 0.82 |
| Example 14 | 32.03 | 0.71 |
| Example 15 | 30.75 | 1.03 |
| Example 16 | 33.63 | 0.74 |
| Example 17 | 34.30 | 0.83 |
| Example 18 | 34.59 | 0.63 |
| Example 19 | 33.68 | 0.62 |
| Example 20 | 35.28 | 0.65 |
| Example 21 | 35.95 | 0.74 |
| Example 22 | 48.57 | 1.11 |
| Example 23 | 95.90 | 0.83 |

Experimental Example 4. Injectability Experiment of Sustained-Release Microparticle Injection Formulation Containing Deslorelin This experiment was conducted to determine the preferred average particle size of the microspheres through the measurement of the microsphere administration and recovery rate. The specific experimental procedure is as follows.

60 mg of the microspheres of Comparative Examples and Examples shown in Table 6 below were weighed, placed in a 1.5 mL vial, and mixed with 0.8 mL of distilled water. Using a 1 mL syringe equipped with a 25G injection needle, the microsphere dispersion was recovered as much as possible, and then the 1.5 mL vial was dried, and the weight of the non-recovered microspheres was measured. The recovery rate was calculated by dividing the weight of the microsphere excluding the measured weight of the non-recovered microsphere by 200 mg of the initial use amount of microsphere.

TABLE 6

Results of injectability experiment of deslorelin-containing microspheres

| Sample | Recovery rate (%) |
|---|---|
| Example 18 | 92.1 |
| Example 19 | 91.8 |
| Comparative Example 6 | 53.0 |
| Comparative Example 8 | 93.5 |
| Comparative Example 9 | 5.6 |
| Comparative Example 10 | 84.2 |
| Comparative Example 13 | 94.6 |

According to the above results, Example 18, Example 19, Comparative Example 8, Comparative Example 10, and Comparative Example 13 are examples in which the particle size is 100 μm or less and also the span value is 1.2 or less, and in the experiment of recovery rate using a syringe equipped with a 25G injection needle, it showed a high recovery rate from a minimum of 84.2% (w/w) to a maximum of 94.6% (w/w). However, even if it has a low span value as in Comparative Example 9, it was confirmed that when the average particle size exceeded 100 μm, the microspheres blocked the injection needle and were not recovered smoothly. Further, even if the average particle size is 100 μm or less as in Comparative Example 6, when the span value is 1.2 or more, the particle size is not uniform, and the recovery rate of the microsphere was considerably low with about 50% (w/w).

As a result, both the particle size and the span value affect the injectability, and in particular, when the particle size is 100 μm or less and the span value is 1.2 or less, it was confirmed that it has relatively more excellent injectability than the microspheres that were not so.

Experimental Example 5. Pharmacokinetic Experiment After a Single Subcutaneous Administration in Sprague-Dawley Rat After the sustained-release microparticle injection formulation containing deslorelin was administered to rats to evaluate its pharmacokinetics, the concentration of deslorelin in blood over time was measured. The microspheres were measured so that the dose of deslorelin was 4.7 mg/head, dispersed in a 0.3 mL suspension, and then injected subcutaneously into Sprague Dawley rats. 0.5 mL blood was collected at pre-planned time intervals, and the concentrations of deslorelin and testosterone in blood were measured using LC-MS/MS.

The results of the pharmacokinetic experiments in rats of the formulations prepared in Comparative Examples and Examples were converted into cumulative release rates relative to AUC (area under the curve) and summarized in Table 7 below.

TABLE 7

Results of pharmacokinetic experiment after a single subcutaneous administration in Sprague-Dawley rat

| Time (Day) | | 0 | 0.042 | 0.125 | 1 | 4 | 7 |
|---|---|---|---|---|---|---|---|
| Example 2 | Cumulative | 0 | 0.347 | 1.266 | 4.151 | 8.143 | 12.134 |
| Example 4 | release rate | 0 | 0.255 | 1.141 | 6.136 | 11.480 | 15.612 |
| Example 6 | of drugs in | 0 | 0.210 | 0.915 | 4.411 | 7.404 | 10.025 |
| Example 9-2 | the body (%) | 0 | 0.403 | 1.393 | 3.894 | 10.454 | 18.525 |
| Example 19 | | 0 | 0.462 | 1.750 | 6.562 | 12.379 | 15.536 |
| Example 22 | | 0 | 0.416 | 1.539 | 5.692 | 13.045 | 19.571 |
| Example 23 | | 0 | 0.308 | 1.234 | 5.010 | 8.342 | 10.045 |
| Comparative Example 1-1 | | 0 | 0.536 | 2.059 | 8.041 | 13.241 | 14.127 |
| Comparative Example 2 | | 0 | 0.622 | 2.341 | 8.693 | 13.600 | 13.911 |
| Comparative Example 5 | | 0 | 0.461 | 1.686 | 5.567 | 8.061 | 8.314 |
| Comparative Example 7 | | 0 | 0.266 | 1.082 | 4.990 | 13.175 | 23.950 |

| | | 14 | 21 | 28 | 42 | 56 | 70 |
|---|---|---|---|---|---|---|---|
| Example 2 | Cumulative | 19.958 | 25.190 | 27.386 | 30.763 | 34.668 | 37.601 |
| Example 4 | release rate | 25.411 | 32.112 | 36.901 | 46.006 | 53.106 | 57.765 |
| Example 6 | of drugs in | 23.078 | 37.258 | 43.747 | 49.428 | 51.724 | 53.522 |
| Example 9-2 | the body (%) | 33.544 | 44.246 | 50.507 | 57.135 | 60.682 | 65.335 |
| Example 19 | | 20.666 | 26.078 | 29.792 | 37.208 | 48.734 | 58.450 |
| Example 22 | | 38.017 | 52.133 | 56.051 | 61.574 | 66.587 | 71.122 |
| Example 23 | | 12.663 | 19.381 | 29.860 | 49.166 | 59.514 | 64.631 |
| Comparative Example 1-1 | | 14.127 | 14.127 | 14.127 | 14.127 | 14.127 | 14.661 |
| Comparative Example 2 | | 13.961 | 13.961 | 14.608 | 20.524 | 34.348 | 50.133 |
| Comparative Example 5 | | 10.243 | 17.375 | 32.407 | 68.275 | 90.115 | 97.023 |
| Comparative Example 7 | | 63.174 | 92.775 | 97.522 | 99.517 | 99.836 | 100 |

| Time (Day) | | 84 | 98 | 112 | 126 | 140 | 154 |
|---|---|---|---|---|---|---|---|
| Example 2 | Cumulative | 42.562 | 50.622 | 60.684 | 72.052 | 81.058 | 86.923 |
| Example 4 | release rate | 62.261 | 68.500 | 75.817 | 82.523 | 87.543 | 91.177 |
| Example 6 | of drugs in | 57.083 | 63.385 | 70.568 | 77.698 | 83.425 | 87.432 |
| Example 9-2 | the body (%) | 72.183 | 77.480 | 80.212 | 83.635 | 87.405 | 90.731 |
| Example 19 | | 63.222 | 68.066 | 72.284 | 76.708 | 81.117 | 85.287 |
| Example 22 | | 75.524 | 79.024 | 82.515 | 85.903 | 88.936 | 91.823 |
| Example 23 | | 68.537 | 71.631 | 74.767 | 77.616 | 80.490 | 83.642 |
| Comparative Example 1-1 | | 20.544 | 38.713 | 59.701 | 74.461 | 85.119 | 90.569 |
| Comparative Example 2 | | 61.272 | 69.617 | 76.555 | 82.435 | 87.069 | 89.996 |
| Comparative Example 5 | | 99.494 | 100 | 100 | 100 | 100 | 100 |
| Comparative Example 7 | | 100 | 100 | 100 | 100 | 100 | 100 |

| Time (Day) | | 168 | 182 | 196 | 210 | 224 | 252 |
|---|---|---|---|---|---|---|---|
| Example 2 | Cumulative | 91.814 | 95.803 | 98.485 | 99.597 | 99.805 | 100 |
| Example 4 | release rate | 94.135 | 96.879 | 98.974 | 99.709 | 99.880 | 100 |
| Example 6 | of drugs in | 91.414 | 95.136 | 97.773 | 99.094 | 99.653 | 100 |
| Example 9-2 | the body (%) | 93.604 | 96.241 | 98.325 | 99.553 | 99.940 | 100 |
| Example 19 | | 90.079 | 95.223 | 98.362 | 99.441 | 99.968 | 100 |
| Example 22 | | 94.772 | 97.743 | 99.441 | 99.792 | 99.903 | 100 |
| Example 23 | | 86.974 | 89.750 | 91.637 | 93.729 | 95.988 | 100 |
| Comparative Example 1-1 | | 93.771 | 96.331 | 97.599 | 98.724 | 99.550 | 100 |
| Comparative Example 2 | | 92.736 | 95.476 | 97.404 | 98.857 | 99.601 | 100 |
| Comparative Example 5 | | 100 | 100 | 100 | 100 | 100 | 100 |
| Comparative Example 7 | | 100 | 100 | 100 | 100 | 100 | 100 |

From the above results, it was confirmed that in the case of the biodegradable polymeric microsphere formulation containing deslorelin prepared from a single polymer, the release of drugs in the formulation prepared using polylactide-co-glycolide was too short. It was confirmed that the formulations prepared using polylactide have a relatively increased duration of maintaining the blood concentration of drugs, but within the initial 1 month after administration, not only the period during which the drug was hardly released after the initial release occurred, but also the bioavailability was remarkably low.

However, in the case of the formulation prepared in Examples of the present disclosure to overcome these problems, it was confirmed that the drug was continuously released for 6 months or more after administration. The release pattern of these drugs are not particularly limited, and it was confirmed that preferably, 10% or more of the drug is released within 1 month after administration and 85% or more of the drug is released within 6 months after administration, more preferably, 15% or more of the drug is released within 1 month after administration, 40% to 80% within 3 months after administration, and 85% or more within 6 months after administration, and most preferably, 15% to 70% of the drug is released within 1 month after administration of microsphere, 40% to 80% of the drug is released within 3 months after administration, and 90% or more of the drug is released within 6 months after administration.

The invention claimed is:

1. A microsphere injection formulation comprising:
   (i) sustained-release microspheres comprising 5 to 25% by weight of deslorelin acetate based on the total weight of the microspheres, and two polymers consisting of polylactide (PLA) and poly (lactide-co-glycolide) (PLGA), or
   (ii) two or three types of sustained-release microspheres, wherein the two or three types of microspheres comprise 5 to 25% by weight of deslorelin acetate based on the total weight of the microspheres, and one or two polymers which are independently contained in the two or three types of the microspheres, wherein the one polymer in (ii) is PLGA or PLA, and the two polymers in (ii) consist of PLGA and PLA;

wherein the PLA in (i) and (ii) is included in an amount of 50 to 90% by weight based on the total weight of the polymers;

and the PLGA in (i) and (ii) has a lactide: glycolide molar ratio of 50:50 to 75:25;

wherein an intrinsic viscosity of the PLA and PLGA in (i) and (ii) is 0.16-1.2 dL/g and 0.14-0.44 dL/g, respectively;

an average particle size of the microsphere in (i) or (ii) is 10 μm to 100 μm;

a span value of the microsphere in (i) or (ii) is 1.2 or less; and the microsphere releases less than 10% of deslorelin acetate on day 1, 25-60% on day 28, and more than 85% on day 182 after administration.

2. The microsphere injection formulation according to claim 1, wherein the microsphere injection formulation containing deslorelin acetate is administered to an animal via a subcutaneous or intramuscular route.

3. The microsphere injection formulation according to claim 1, wherein a recovery rate upon injection of the microsphere is 80 to 100% when measured using a 1 ml syringe equipped with a 25G injection needle.

* * * * *